United States Patent [19]

Bechgaard

[11] Patent Number: 4,610,881

[45] Date of Patent: Sep. 9, 1986

[54] PROTECTIVE COMPOSITION WITH PENETRATING CARRIER

[76] Inventor: Carl C. Bechgaard, Bredballe, DK 7100 Vejle, Denmark

[21] Appl. No.: 348,358

[22] Filed: Feb. 12, 1982

Related U.S. Application Data

[63] Continuation-in-part of Ser. No. 292,994, Aug. 14, 1981, abandoned.

[51] Int. Cl.$^4$ ............................................. A61K 33/22
[52] U.S. Cl. ................................................... 424/148
[58] Field of Search ........................................ 424/148

[56] References Cited

U.S. PATENT DOCUMENTS

| | | | |
|---|---|---|---|
| 2,968,590 | 1/1961 | Ploquin | 424/148 |
| 2,998,310 | 8/1961 | O'Brien | 71/69 |
| 3,305,298 | 2/1967 | Chapman et al. | 424/148 |
| 3,993,752 | 11/1976 | Stutz | 424/148 |

FOREIGN PATENT DOCUMENTS 0937766  9/1963  United Kingdom .

*Primary Examiner*—Donald B. Moyer
*Assistant Examiner*—John W. Rollins, Jr.
*Attorney, Agent, or Firm*—W. R. Hulbert; Timothy A. French

[57] ABSTRACT

In a composition for application to a porous substrate, e.g. timber, to protect it e.g. from attack by insects or fungi, there is a protective substance, e.g. a boron-rich compound (containing at least 25% by weight $B_2O_3$) in a liquid carrier which according to the invention is a hygroscopic liquid, preferably ethylene glycol. When applied to wood the composition with the glycol carrier penetrates the outer layers of the wood more rapidly than a comparable composition with water as carrier.

7 Claims, No Drawings

PROTECTIVE COMPOSITION WITH PENETRATING CARRIER

This application is a continuation-in-part of application Ser. No. 292,994, filed Aug. 14, 1981, now abandoned.

This invention relates to a carrier for transporting a protective material into a substrate which said material protects from deterioration. Examples of such materials are insecticides, herbicides, fire-retardants, and fungicides. The invention provides a composition for application to a porous substrate to protect it. The prime example of such a substrate is wood, including wood-base building materials such as particle-board and chipboard; brickwork, concrete and mortar are other materials liable to harbour fungal infection which can be treated with a composition according to the invention.

The invention is of particular importance for the transport of biologically active materials and notably insecticides and fungicides into wood either as a remedial treatment for existing insect attack or fungus decay or as a prophylactic treatment against future infection. Thus in a particular aspect the invention relates to the treatment of wood to reduce its susceptibility to wood-destroying insects and decay-causing fungi; in this aspect the invention provides a composition for such treatment of wood.

Insecticides, herbicides, fungicides and similar biologically active materials are often applied to substances which they are intended to protect from insect, herbal or fungal infection in the form of a solution of said active material in a liquid. Examples of liquids widely used carriers for biologically active materials are water, white spirit or other petroleum fraction, and alcohols of 3 or more carbon atoms. The carriers commonly employed for this purpose have disadvantages—some do not penetrate rapidly into the substrate, while other present fire risk or are otherwise objectionable on the ground of damage to the enviroment. It is an object of this invention to provide a class of alternative carriers which are less subject to these disadvantages. It is a special object of this invention to provide a composition for application to wood in which the carrier for the actively protective material penetrates the wood more rapidly than does water.

According to the present invention the carrier for a biologically active material in a composition for application to a substrate to protect it is a hygroscopic liquid. It appears possible that the liquid, being hygroscopic, is drawn into a substrate by its affinity with residual moisture there, whether in moist wood, in brickwork, in mortar, or in water bonded to the cellulose in apparently dry wood.

The hygroscopic liquids which have been found particularly useful for this purpose are glycols, the most preferred liquid is ethylene glycol and its hygroscopic derivatives.

The biologically active material for which these carriers are especially suitable are boron-rich compounds, by which is meant compounds having a content of combined boron equivalent to more than 25%, preferably more than 35%, by weight $B_2O_3$. Examples of such compounds are boric oxide itself, boric acid, borax (sodium tetraborate decahydrate), borax pentahydrate, anhydrous borax, and various potassium and ammonium borates. Another such compound, which has been widely used for the preservation of timber and which is the preferred active ingredient in the composition of the present invention, is disodium octaborate, a water-soluble powder of the approximate composition $Na_2B_8O_{13}4H_2O$. This is available in the United Kingdom under the Registered Trade Mark "Timbor" and in the United States of America under the Trade Mark "Polybor".

The preparation of disodium octaborate hydrate is described in U.S. Pat. No. 2,998,310 (Aug. 29 1961).

British Patent Specification No. 937,766 shows a composition for application to timber to make it flame-retardant and incidentally immune to insect and fungus attack; the active ingredient in the composition is a sodium octaborate and the carrier i.e. the predominant solvent, is water, and the composition may include a small amount, 1–5%, of ethylene glycol as a humidifying agent. Timbor (or Polybor) is recommended only for application to green timber, usually as an aqueous paste containing up to 40% of active ingredient. However, boron-rich compounds when applied to timber from solution in water diffuse into the timber only slowly, over some weeks, to the high loading considered necessary for full protection of the timber, and may leach out fairly readily if not protected from contact with water after application. They are recommended for the treatment of freshly-sawn timber before it is used in building, but not recommended for the treatment of wood in a building, and are specifically contra-indicated for conditions involving ground contact and for external use except where protected by paint. With a composition containing a glycol as carrier according to the present invention we have found it possible to achieve a rapid penetration of boron-rich compounds into wood, by simple brushing or dipping techniques even without use of vacuum or pressure to promote penetration, and that high amounts of boron-rich compound can be introduced. Compositions of the present invention can successfully be applied to wood additional to freshly-sawn timber, e.g. as a remedial treatment for infection.

Thus the present invention, more narrowly stated, provides a composition for application to timber to preserve it, of the type which comprises a carrier and a biologically active agent which is a boron-rich material in amount at least 15% by weight of composition. (By a "boron-rich material" is meant a material containing at least 35% by weight of boron calculated as $B_2O_3$).

According to the present invention, however, the carrier is not water but is a hygroscopic liquid capable of forming a stable, concentrated solution with the biologically active agent.

The hygroscopic liquids found best are glycols or hygroscopic liquid derivatives of glycols. The especially preferred carrier is ethylene glycol. Other readily available glycols such as hexylene glycol and propanediol form solutions with a boron-rich compound which are inconveniently viscous. The glycol or other hygroscopic liquid, to be a carrier for the active ingredient, should comprise at least 50% by weight of itself-plus-active ingredient, and preferably at least 50% by weight of total composition.

We have found that a solution consisting of 60% by weight ethylene glycol and 40% by weight sodium octaborate is unexpectedly stable at temperatures as low as $-20°$ C., though it is necessary to heat the mixture to $60°$ to effect dissolution. Even with ethylene glycol as the carrier, such a solution may be rather viscous for application to timber by brushing or spraying and it can then be thinned with a diluent, notably with water.

However, if water or other diluent is present in the composition of the invention, its amount should not exceed 50% by weight of carrier-plus-active agent and preferably not exceed 20%. We have found that addition of as little as 25% by weight of water to the relatively concentrated glycol solution of the active ingredient may cause the active ingredient to precipitate, and though the precipitate can be re-dissolved by heating the mixture, this is inconvenient.

More importantly, the glycol or other hygroscopic liquid which is the carrier for the active ingredient in the composition of this invention appears to force its way rapidly into the surface portion of wood to which it is applied, whereas an aqueous solution of the active ingredient diffuses more slowly. Dilution of the glycol solution with water should, therefore, be minimized to the level needed to achieve a workable viscosity.

Dilution of the glycol solution with ethanol, e.g. 5% of ethanol, can marginally reduce the penetration time but ethanol is a fire hazard.

The impregnation of wood products with polyethylene glycol in order to make the wood dimensionally stable (i.e. to prevent shrinkage when the wood dries out) has previously been proposed, and with such proposal there has been suggested the simultaneous incorporation of an insecticidal, fungicidal or fire-retarding agent of which borax is one example. In that case, however, the aim has been to stabilise the timber, and the presence of the insecticidal or other agent, in small amount, has been merely incidental. In the composition of the present invention the liquid, e.g. monoethylene glycol, serves as a mere carrier for the active ingredient, which must therefore be present in substantial amount—at least 15% by weight of composition.

A typical composition according to the present invention comprises by weight:

| Disodium octaborate | 40% |
|---|---|
| Glycol | 60% |

A preferred composition according to the invention comprises by weight:

| Disodium octaborate | 40% |
|---|---|
| Glycol | 51% |
| Water | 9% |

The composition of this invention can be prepared by simply mixing the active ingredient, e.g. disodium octaborate, with the carrier, e.g. ethylene glycol; for a solution containing a large amount such as the preferred 40% of the active ingredient it is necessary to heat the mixture to e.g. 60° C. in order to effect dissolution, but once dissolved the solute shows no tendency to precipitate when cooled. This suggests that the preferred composition of this invention may be a stable supersaturated solution.

The concentration of active ingredient may be varied as desired to achieve a desired concentration of boron. The most suitable composition contains more than 20% by weight of boron calculated as $B_2O_3$, compositions containing 15% or even 10% are still, though less, effective. Thus a higher concentration of borax (36.5% $B_2O_3$) is needed than of Timbor, (67.1% $B_2O_3$). In general, however, the highest reliably stable concentration of $B_2O_3$ is needed, which makes it preferable to use boron-rich materials having a $B_2O_3$ content of 60% or more.

A composition of the invention may be applied to wood by any desired method, e.g. immersion, by spraying or most conveniently by brushing. It is an advantage of this invention that more complicated techniques for effecting penetration, such as pressure or the vacuum-vacuum process, are not generally needed though they may be used for compositions of this invention if desired. We have measured the rate of penetration of compositions according to the invention when brushed onto the surface of wood (pine sapwood of moisture content 19-20%; spruce and other softwoods and even hardwoods such as oak and beech react similarly) at the rate of 160 grams of composition per square meter of wood. Compositions containing 20% and 40% by weight of active ingrediant both penetrate to a depth of 3-5 mm within 24 hours. The penetration is substantially uniform, i.e. there is no marked concentration gradient, and the glycol carrier and borate active ingredient penetrate equally, i.e. there is no immediate separation of solute from solvent. Subsequently the boron-rich material diffuses more deeply into the wood, the depth of penetration being at least doubled in the course of twenty weeks in wood of 15-20% moisture content, though the carrier does not diffuse so far. The penetration of the carrier can be observed by inclusion of a fruit dye therein, and of the borate by reaction with turmeric.

It therefore appears possible that the glycol carrier serves to draw the borate rapidly into the outer portion of the wood near the surface, and that once a reservoir is thus established subsequently penetration is by the same mechanism as causes the slow diffusion of borate as disclosed in British specification No. 937766.

The more concentrated solution, e.g. 40% as opposed to 20%, appears to penetrate the wood more quickly than the less concentrated, during the initial treatment of the wood with the composition, and further penetration can be achieved by a second application. Thus in some cases it may be advantageous to make two applications of a less concentrated solution to achieve the same loading. With a single application of the 40% composition it is possible to incorporate borate into the outer 5 mm of wood evenly at the rate of 12 kg/m$^3$ within 24 hrs of application—diffusion to greater depth follows.

It is well established that the presence of borates (such as the sodium octaborate preferred for this invention) in wood protects the wood from fungal decay and insect attack. Moreover, the composition set out above containing 40% sodium octaborate, ethylene glycol and a small amount of water has been used in practice and found effective in conditions where other remedial treatments have been tried and failed. Fungus species which have been controlled in infected wood in buildings include *Coniophora cerebella, C. putriana, Lenzitis sapiara, L. tribium, Merulius lacrymans, Poria vaporaria* and *Paxillus* sp.; in each case severely infected wood was treated with a composition according to the invention and the fungus growth died. The treatment composition penetrated also the surrounding brickwork and concrete and killed fungus which had spread there from the wood.

Timbers in buildings infested with *Xestobium rufivollosum, Anobium punctatum, A. mollis* and *Callidium viollacem* have been sprayed or brushed with the composition according to the invention and in each case all sign of infection, i.e. fresh larva dust or flight holes, ceased.

The composition of this invention wherein the active material is a boron-rich compound has the unexpected effect of preparing the surface of wood for subsequent painting, and thus serves as a priming composition.

I claim:

1. A liquid composition for application to a porous substrate liable to harbor infection, consisting essentially of:
   (a) as active ingredient, a material containing combined boron in an amount equivalent to more than 25 percent $B_2O_3$ by weight of the material, the quantity of active ingredient being sufficient to provide at least 10 percent by weight of combined boron, calculated as $B_2O_3$, by weight of the composition;
   (b) ethylene glycol as liquid carrier for the active ingredient in an amount of at least 50 percent by weight based on the weight of the composition; and optionally
   (c) water in an amount of at most 20 percent by weight of the composition.

2. A composition according to claim 1 in which said active ingredient is one containing boron in an amount equivalent to more than 35% $B_2O_3$.

3. A composition according to claim 2 in which the active ingredient is selected from (i) boric oxide, (ii) borax, (iii) borax pentahydrate, (iv) anhydrous borax and (v) a disodium octaborate.

4. A composition according to claim 3 in which the active ingredient is a disodium octaborate in an amount 20 to 40% by weight of composition.

5. A composition according to claim 1 in which the active ingredient is present in an amount 20 to 40% by weight of the active ingredient (a) plus the glycol (b).

6. A composition according to claim 1 in which the quantity of active ingredient is sufficient to provide at least 15% of combined boron, calculated as $B_2O_3$, by weight of composition.

7. A method of treating timber to reduce its susceptibility to wood-destroying insects and decay-causing fungi which comprises effecting penetration into the wood of a composition consisting essentially of:
   (a) as active ingredient, a material containing combined boron in an amount equivalent to more than 25 percent $B_2O_3$ by weight of the material, the quantity of active ingredient being sufficient to provide at least 10 percent by weight of combined boron, calculated as $B_2O_3$, by weight of the composition;
   (b) ethylene glycol as liquid carrier for the active ingredient in an amount of at least 50 percent by weight based on the weight of the composition; and optionally
   (c) water in an amount of at most 20 percent by weight of the composition.

* * * * *